United States Patent
Brandt

(10) Patent No.: US 11,918,438 B2
(45) Date of Patent: *Mar. 5, 2024

(54) PREDICTING THE DEVELOPMENT OF A DENTAL CONDITION

(71) Applicant: 3SHAPE A/S, Copenhagen K (DK)

(72) Inventor: Henrik John Brandt, Copenhagen NV (DK)

(73) Assignee: 3SHAPE A/S, Copenhagen K (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/533,163

(22) Filed: Nov. 23, 2021

(65) Prior Publication Data

US 2022/0079718 A1 Mar. 17, 2022

Related U.S. Application Data

(63) Continuation of application No. 16/305,709, filed as application No. PCT/EP2017/062825 on May 29, 2017, now Pat. No. 11,207,161.

(30) Foreign Application Priority Data

May 30, 2016 (DK) .............................. PA201670374

(51) Int. Cl.
*G06K 9/00* (2022.01)
*A61C 9/00* (2006.01)
(Continued)

(52) U.S. Cl.
CPC ............ *A61C 9/0053* (2013.01); *G06T 17/00* (2013.01); *G16H 30/20* (2018.01); *G16H 50/50* (2018.01);
(Continued)

(58) Field of Classification Search
CPC .............. G06T 17/00; G06V 2201/031; G06V 2201/12
See application file for complete search history.

(56) References Cited

U.S. PATENT DOCUMENTS

| | | | |
|---|---|---|---|
| 3,050,534 A | 8/1962 | Albert et al. | |
| 5,769,074 A | 6/1998 | Barnhill et al. | |

(Continued)

FOREIGN PATENT DOCUMENTS

| | | | | |
|---|---|---|---|---|
| CA | 2816368 A1 * | 5/2012 | ......... | A61C 13/0004 |
| EP | 3050534 A1 * | 8/2016 | ........... | A61B 5/0035 |

(Continued)

OTHER PUBLICATIONS

A New method—A Feasibility Study. Karl Martin Lehmann et al., ResearchGat, 2012, pp. 50-54 (Year: 2012).*

(Continued)

*Primary Examiner* — Jayesh A Patel
(74) *Attorney, Agent, or Firm* — Buchanan Ingersoll & Rooney PC

(57) ABSTRACT

Disclosed is method, a user interface, a computer program product and a system for predicting future development of a dental condition of a patient's set of teeth, wherein the method comprises:—obtaining two or more digital 3D representations for the teeth recorded at different points in time;—deriving based on the obtained digital 3D representations a formula expressing the development of the dental condition in terms of at least one parameter as a function of time; and—predicting the future development of the condition based on the derived formula.

23 Claims, 8 Drawing Sheets

(51) Int. Cl.
*G06T 17/00* (2006.01)
*G16H 30/20* (2018.01)
*G16H 50/50* (2018.01)

(52) U.S. Cl.
CPC .... *G06V 2201/031* (2022.01); *G06V 2201/12* (2022.01)

(56) References Cited

U.S. PATENT DOCUMENTS

| | | | |
|---|---|---|---|
| 5,779,634 | A | 7/1998 | Ema et al. |
| 6,471,511 | B1 | 10/2002 | Chishti et al. |
| 6,949,240 | B2 | 9/2005 | Sagel et al. |
| 7,069,186 | B2 | 6/2006 | Jung et al. |
| 7,736,857 | B2 | 6/2010 | Denny et al. |
| 8,073,212 | B2 * | 12/2011 | Gerlach ............ A61B 5/0088 382/128 |
| 9,763,757 | B2 * | 9/2017 | Llop ................ A61C 13/0004 |
| 9,770,217 | B2 * | 9/2017 | Sandholm ............ A61B 6/5205 |
| 10,098,715 | B2 * | 10/2018 | Joshi ........................ A61B 6/14 |
| 10,835,361 | B2 * | 11/2020 | Fisker .................... A61B 5/1111 |
| 11,207,161 | B2 * | 12/2021 | Brandt .................... G16H 30/20 |
| 2004/0219111 | A1 | 11/2004 | Kim et al. |
| 2005/0095562 | A1 | 5/2005 | Sporbert et al. |
| 2005/0192835 | A1 | 9/2005 | Kuo et al. |
| 2006/0062442 | A1 | 3/2006 | Arnaud et al. |
| 2006/0063135 | A1 | 3/2006 | Mehl |
| 2006/0099547 | A1 | 5/2006 | Knopp |
| 2008/0021584 | A1 | 1/2008 | Whaite et al. |
| 2010/0167225 | A1 | 7/2010 | Kuo |
| 2010/0279248 | A1 | 11/2010 | Mourad et al. |
| 2013/0054190 | A1 | 2/2013 | Kadobayashi et al. |
| 2013/0216971 | A1 | 8/2013 | Friddell |
| 2014/0329194 | A1 | 11/2014 | Sachdeva et al. |
| 2015/0017101 | A1 * | 1/2015 | Schnabelrauch .. A61K 49/0069 424/9.1 |
| 2015/0313559 | A1 | 11/2015 | Ortega et al. |
| 2015/0320320 | A1 | 11/2015 | Kopelman et al. |
| 2015/0342545 | A1 | 12/2015 | Bergersen |
| 2016/0004811 | A1 * | 1/2016 | Somasundaram ...... G06T 19/20 703/11 |
| 2016/0038092 | A1 | 2/2016 | Golay |
| 2016/0135925 | A1 * | 5/2016 | Mason .................. A61C 7/002 703/2 |
| 2016/0220173 | A1 | 8/2016 | Ribnick et al. |
| 2016/0220200 | A1 * | 8/2016 | Sandholm ............ A61B 5/0088 |
| 2018/0132982 | A1 * | 5/2018 | Nikolskiy ............... G06T 17/00 |
| 2019/0060042 | A1 * | 2/2019 | Fisker .................. A61C 9/0053 |
| 2019/0328234 | A1 * | 10/2019 | Seibel ...................... A61B 1/24 |
| 2020/0281697 | A1 | 9/2020 | Brandt |

FOREIGN PATENT DOCUMENTS

| | | | | |
|---|---|---|---|---|
| EP | 3050534 | A1 | | 8/2016 |
| UA | 43693 | U | * | 8/2009 |
| UA | 49378 | U | * | 4/2010 |
| WO | WO-2014027024 | A2 | * | 2/2014 ............. A61C 11/00 |
| WO | WO-2014069934 | A1 | * | 5/2014 ............. A61C 13/34 |
| WO | 2015011173 | A1 | | 1/2015 |
| WO | WO-2016003787 | A1 | * | 1/2016 ........... A61B 5/0088 |
| WO | WO-2017144647 | A1 | * | 8/2017 ........... A61B 5/0088 |

OTHER PUBLICATIONS

Tooth colour: a review of the literature, Andrew Joiner, Elsevier, 2004, pp. 3-12 (Year: 2004).*
Developement and evaluation of a method in vitro to study the effectiveness of tooth bleaching, M. Sulleman et al., Elsevier, 2003, pp. 415-422 (Year: 2003).*
Microsurgical Treatment of Gingival Recession: A Controlled Clinical Study, Luca Francetti et al., 2005, pp. 181-188 (Year: 2005).*
Coronally advanced flap versus connective tissue graft in the treatment of multiple gingival recessions: a split-mouth study, Pini-Prato GP et al., 2010, pp. 644-650 (Year: 2010).*
International Search Report (PCT/ISA/210) dated Oct. 2, 2017, by the European Patent Office as the International Searching Authority for International Application No. PCT/EP2017/062825.
Written Opinion (PCT/ISA/237) dated Oct. 2, 2017, by the European Patent Office as the International Searching Authority for International Application No. PCT/EP2017/062825.
Bauer, JG, et al., "Predictor Model of Root Caries in Older Adults: Reporting of Evidence to the Translational Evidence Mechanism", The Open Dentistry Journal, 2010, pp. 124-132, vol. 4.
Betina Tolcachir, "Measuring color change of tooth enamel by in vitro remineralization of white spot lesion", Journal of Oral Research, 2015, pp. 371-377.
Eloisa Andrade De Paula, et al., "In-office bleaching with a two- and seven-day intervals between clinical sessions: A randomized clinical trial on tooth sensitivity", 2015, pp. 424-429, Elsevier.
Office Action issued in corresponding European Patent Application No. 17727180.6-1126, dated Apr. 1, 2021. (9 pages).
Joiner, Andrew, et al., "A review of tooth colour and whiteness", Journal of Dentistry, 2008, pp. s2-s7, vol. 362, Elsevier.
Joiner, Andrew, "Tooth colour: a review of the literature", 2004, pp. 3-12, Elsevier.
Jurriaans, Robrecht, "3D-VITA", Universiteit van Amsterdam, 2014, pp. 1-14.
K.M. Lehmann, et al., "A New Method for Volumetric Evaluation of Gingival Recessions: A Feasibility Study", Journal of Periodontology, Jan. 2012, pp. 50-54, vol. 83, No. 1.
Ning Dai, et al., "3D Simulation Moedling of the Tooth Wear Process", PLOS One, 2015, pp. 1-13, vol. 10, No. 8.
Sulieman, M., et al., "Development and evaluation of a method in vitro to study the effectiveness of tooth bleaching", Journal of Dentistry, 2003, pp. 415-422, vol. 31, Elsevier.
Tolcachir, Betina, et al., "Measuring color change of tooth enamel by in vitro remineralization of white spot lesion", Journal of Oral Research, 2015, pp. 371-377.

* cited by examiner

100

```
┌─────────────────────────────────────────────────────┐
│ Obtaining digital 3D representations for the teeth  │  101
│        recorded at different points in time         │
└─────────────────────────────────────────────────────┘
                          │
                          ▼
┌─────────────────────────────────────────────────────┐
│  Deriving a formula expressing the development of the│
│  dental condition in terms of at least one parameter as a │  102
│                   function of time                  │
└─────────────────────────────────────────────────────┘
                          │
                          ▼
┌─────────────────────────────────────────────────────┐
│   Predicting the future development of the condition│  103
│              based on the derived formula           │
└─────────────────────────────────────────────────────┘
```

Fig. 1A

PREDICTING THE DEVELOPMENT OF A DENTAL CONDITION

CROSS REFERENCE TO RELATED APPLICATIONS

The present application is a continuation of U.S. patent application Ser. No. 16/305,709, filed on Nov. 29, 2018, which is a national stage of PCT/EP2017/062825, filed on May 29, 2017, which claims priority of Danish Patent Application No. PA201670374, filed on May 30, 2016, the entire disclosures of which are incorporated herein by reference.

TECHNICAL FIELD

This invention generally relates to predicting the development of a dental condition of a patient's teeth. More particularly, the invention relates to predicting the development based on digital 3D representations and diagnostic data of the patient's teeth obtained at different points in time.

SUMMARY

Disclosed is a method for predicting future development of a dental condition of a patient's set of teeth, wherein the method comprises:
  obtaining two or more digital 3D representations for the teeth recorded at different points in time;
  deriving based on the obtained digital 3D representations a formula expressing the development of the dental condition as a function of time; and
  predicting the future development of the condition based on the derived formula.

Software for implementing the method can also provide a means for illustrating to the patient how the dental condition may evolve unless a treatment is made and thus will be a significant collaboration tool between the doctor and the patient. In many cases seeing the predicted development will convince the patient that a suggested treatment will be of great value for him/her.

Often a dental condition, such as tooth wear or gingiva recession, develops over a period of months or years. Accordingly, the digital 3D representations used for deriving the formula are often acquired over several months or years and the disclosed embodiments may provide that the development of the dental condition can be predicted for the months or years to come. Accordingly, the points in time where the digital 3D representations are obtained may be separated by more than 3 months, such as more than 4 months, such as more than 6 months, such as more than 9 months, such as more than 12 months, such as more than 18 months.

Many of the disclosed embodiments are not limited to digital 3D representations of the teeth but can also be applied to digital data sets in general, such as 2D color images of the teeth, and using such digital data sets for predicting the future development of the dental condition.

In some embodiments, the formula expresses the development of the dental condition in terms of at least one parameter. The parameter relates to or expresses a property of the teeth, such as tooth color or shape, gingiva margin profile, etc.

The derived formula can then provide an estimate of the change in the parameter over time, i.e. what the value of the parameter is expected to be at a future point in time, and thus of the future development of the dental condition unless preventive actions are taken or a behavior of the patient is changed.

In some embodiments, the parameter is expressed or provided as a distribution over at least part of the teeth.

The values of the parameter may be determined for a portion of one tooth, such as for a selected point on or a selected part of the tooth surface. When e.g. predicting future changes in tooth color the operator may e.g. chose to determine the color only for the labial surface of the anterior teeth. When predicting the development of tooth wear the operator may choose to focus on the occlusal surfaces of the teeth since these are most severely influenced by e.g. Bruxism.

The value of the parameter may also be determined and predicted as an average value over a portion of one tooth or over the entire tooth. For example, the color of the labial surface of a tooth may be averaged over the entire labial surface. The average value can also be determined at selected points or parts of the tooth e.g. by dividing the surface into regions for which average color values are determined. The operator may e.g. select such points or parts using a pointing tool such as a computer mouse to indicate the points on a 3D visualization of the tooth or teeth on a computer screen.

The difference in the parameter between two digital 3D representations may be expressed as a difference map. For example, changes in tooth shape and size caused by tooth wear can be expressed as a difference map showing the decrease in the height of the tooth enamel layer.

In such cases, it may also be relevant to determine the point where the maximum value of the parameter is found in the distribution.

The digital 3D representations comprise at least geometrical data expressing the shape of one or more of the patient's teeth and their relative arrangement in the mouth.

In some embodiments, the digital 3D representations further comprise color and/or shade data such that the digital 3D representations also express the color and/or shade profile of the teeth. This provides that changes in the color or shade of the teeth can be monitored, to predict e.g. color and/or shade changes or the development of caries.

In some embodiments, the digital 3D representations further comprise diagnostic data which can provide information relating to various dental conditions such as fluorescence data, IR-transparency data, and/or X-ray data.

Both the geometrical and the color, shade and/or diagnostic data may be obtained for both the patient's teeth and the soft tissue in the mouth, such as the gingiva and gum surface.

In some embodiments, the diagnostic data and the digital 3D representation with the shape data are recorded as separate data sets, e.g. by separate devices. In the context of the current application the phase "deriving based on the obtained digital 3D representations a formula expressing the development of the dental condition in terms a parameter as a function of time" may thus also refer to the situation where parameter values are determined from the diagnostic data and the digital 3D representations are used as reference to provide a spatial correlation between the patient's teeth and the diagnostic data or the parameter values determined therefrom.

In some embodiments, the predicting comprises calculating a predicted value of the parameter for at least one future point in time using the derived formula.

Determining such a predicted value provides the advantage that the dentist can evaluate whether the development of a dental condition related to the parameter will become a problem in the near future.

In some embodiments, the predicting comprises using the derived formula to predict the point in time where the parameter is expected to reach a threshold value. The threshold value may be related to a situation where the condition has reached a stage where the situation is either critical or close to being critical.

Determining this point in time has the advantage that the dentist can inform the patient how soon the dental condition probably will have evolved to become a problem.

In some embodiments, the dental condition relates to tooth wear or acid damages of the teeth and the threshold relates to an expected thickness of the tooth enamel. The expected thickness can e.g. be determined from clinical studies determining an average enamel thickness for humans, optionally dependent on the patient's age, general heath, habits and other parameters influencing the patient's teeth, or from X-ray or Optical Coherence Tomography measurements.

Having the prediction for the development of the dental condition allows the dentist to inform the patient that preventive measures should be considered to prevent further development. When the dental condition relates to bruxism the patient may e.g. consider having a night guard made. The expected point in time may then mark when it is expected that the patient's enamel in the affected region is gone or has become critical thin.

In some embodiments, the parameter relates to tooth color and/or tooth shade and the threshold relates to an acceptable darkening of the teeth or a color change indicating significant caries development.

In some embodiments, the formula is derived from values of the parameter determined for each of the obtained digital 3D representations.

The parameter can e.g. relate to the color of the anterior maxillary teeth and the formula be derived directly from the color values read from each of the digital 3D representations with the formula expressing the change in the color values as a function of time.

In some embodiments, the formula is derived from differences in the parameter determined by comparing the obtained digital 3D representations.

This is e.g. relevant when the condition relates to gingiva recession where there's a change in the shape and position of the gingival margin at the tooth surface. When two digital 3D representations taken at different points in time are compared the relative position of the gingival margins for the two digital 3D representations can be determined and the formula can be derived to predict the future development of the gingival recession.

Another example is tooth wear where the distance between the occlusal surfaces of the compared digital 3D representations can be detected when the digital 3D representations are aligned and provides a measure of the reduction in the depth of the tooth enamel.

A change in the parameter may be determined as an accumulated change relative to a selected digital 3D representation, such as relative to the first digital 3D representation recorded for the patient or relative to a first digital 3D representation recorded after a treatment has ended.

A user interface for performing the steps of the method should preferably allow the operator to select which digital 3D representation defines the zero-point for the development of the parameter and/or which digital 3D representations should be compared when deriving the formula.

Different parameters, such as tooth color, shape or relative positions, can be used in detecting and predicting future development of a dental condition. In some embodiments, the parameter is selected from the group consisting of: tooth color, tooth shade, tooth brightness or lightness, distribution of fluorescence emitted from the teeth, distribution of transparency of the teeth at infrared wavelengths, tooth shape, tooth size, the depth of the tooth enamel, the relative arrangement of the teeth, gingiva color, the shape and/or position of the gingival margin, and the area of the visible tooth surface.

When the patient's teeth are worn, e.g. due to Bruxism, the reduction in the depth of the tooth enamel from one point in time to another can be detected from the digital 3D representations obtained at these points in time, e.g. by aligning and comparing the digital 3D representations. Such a comparison will show the reduction in the depth of the tooth enamel as an offset between the occlusal surfaces of teeth in the digital 3D representations.

When the patient suffers from a gingival recession such a comparison between digital 3D representations can also be used for deriving a formula for the change in the shape and/or position of the gingival margin over time.

In some embodiments, the dental condition is selected from the group of: caries, tooth wear, tooth erosion, darkening of the teeth, gingiva recession, gingival infection or disease, a change in the arrangement of the teeth in the patient's mouth, a relapse of teeth after an orthodontic treatment, and growth of the teeth.

Tooth color can be represented in many different color spaces, such as the L*C*h* color space representing color in terms of Lightness, Chroma and Hue, or in the L*a*b* color space. The L*a*b* color space has the advantage that it is designed to approximate human vision with the L* component closely matches human perception of lightness.

When the digital 3D representations comprise color data the parameter may relate to the color of the teeth and gingiva and/or the shade of the teeth. The shade of the teeth can be derived as the shade in e.g. the VITA Classical or the VITA 3D-Master shade systems with the shortest color distance to the recorded color data. The color distance can e.g. be calculated as the Euclidian distance $\Delta E$ between two points $(L_1^*, a_1^*, b_1^*)$ and $(L_2^*, a_2^*, b_2^*)$ in the L*a*b* color space which is given by:

$$\Delta E = \sqrt[2]{(L_1^* - L_2^*)^2 + (a_1^* - a_2^*)^2 + (b_1^* - b_2^*)^2}$$

The color values, e.g. the L*a*b* values, may be recorded at selected points on the tooth surface, as a distribution over the tooth surface, or as average values over a region of the tooth.

The formula can be derived for the individual color components, e.g. for each of L*, a* and b*, such that the development can be predicted for each individual component. For example, a formula can be determined for development of the L* component such that the change in the lightness/darkness of the teeth over time can be predicted.

When the dental condition relates to a darkening of the teeth, the formula may be derived from the measured Lightness-values (L*) for color data of the different digital 3D representations and provide an estimate of the change in the Lightness-value with time. The derived formula can then provide a prediction of e.g. the darkening of the teeth with time. Based on this prediction the dentist may e.g. advice the patient to have his teeth bleached soon. The formula can also be adjusted to include a bleaching such that the combined effect of the bleaching and darkening in the years to come can be predicted.

A threshold value relating to an acceptable tooth darkening can be set such that the derived formula can give a prediction of when the darkening will reach an unacceptable level.

If the thickness of the enamel of the patient's teeth is reduced e.g. either due to Bruxism or acid induced erosion, the reduction between different points in time can be detected by comparing the teeth portions of the digital 3D representations of the patient's set of teeth.

The reduction in the tooth surface may be determined as an average over the occlusal/incisal surface of the teeth, as a difference map showing the distribution of the tooth wear over the occlusal surface, or as the maximum reduction in the enamel thickness over the tooth surface.

Threshold values can be set with respect to a maximum allowed reduction in the enamel layer thickness in a single point or region on the tooth surface or in an average reduction measured over the tooth surface.

The development of caries can be detected and predicted using different data. One example of such data is the fluorescence emitted when illuminated by light capable of exciting fluorescent materials of the tooth.

For example, the enamel of healthy teeth emits fluorescence in the range of 520-570 nm when illuminated by light with a wavelength of 405 nm. Scattering at a caries lesion however causes a local decrease in this fluorescence such that the intensity of the emitted fluorescence does not have a uniform distribution. The gradual decrease over time in the fluorescence emitted from a particular region of a tooth can be detected by comparing the fluorescence recorded at different points in time. Therefrom a formula for the further development of the caries in that region can then be derived.

Further, certain caries related bacteria, such as *Streptococcus mutans*, produce special metabolites called porphyrins. These porphyrins fluoresce at red wavelengths, such as light in the wavelength range of 620-740 nm, when exposed to a 405 nm light. The increase in the intensity of this fluorescence detected between different visits at the dentist can be used to derive a formula for predicting the development of caries in that region.

The fluorescence data may be provided as a separate 3D data set where the spatial correlation to the digital 3D representation of the teeth is known or where the method comprises determining this correlation.

The development of caries causes changes in the color of the caries infected region. In the initial phase, the tooth surface appears chalky white indicating a demineralization of the enamel. With continued caries development the color turns brown. The fact that the color in the infected region potentially follow a known path in color space provides that the color change can be used for predicting the development of the caries.

Based on color data of digital 3D representations obtained at different points in time a formula for predicting the development of caries can be derived by correlating the colors recorded in the suspected region and the time each color was recorded to the known path. In a standard color systems, such as the L*a*b* and L*C*h* color systems, the color change caused by caries development will often follow a non-straight line in the color space.

The development of caries can also be detected as an increase in the size of the attacked region of the tooth, such that the area of the attached region identified e.g. in fluorescence or color data from the teeth.

In some embodiments, the derived formula comprises a linear portion and/or a polynomial portion and/or a portion representing a step formula, the latter representing e.g. the change in the parameter caused by a treatment. E.g. a formula expressing the future development of the tooth color could include a step change in the tooth darkness caused by a bleaching of the teeth.

In some embodiments, the method comprises generating a predicted digital 3D representation expressing a predicted configuration of the teeth at a future point in time by applying the derived formula on a digital 3D representation of the teeth.

In some embodiments, wherein generating the predicted digital 3D representation comprises applying a distribution of locally derived formula for the development of the dental condition with time. I.e. formulas are derived for several regions on a tooth such that in the predicted digital 3D representation each of these regions can provide a prediction for that particular region.

The predicted digital 3D representation may comprise a distribution of predicted values for any of the parameters such at tooth shape, size, color, shade, brightness or lightness, the depth of the tooth enamel, the relative arrangement of the teeth, gingiva color, and the shape and/or position of the gingival margin.

When generating a predicted digital 3D representation of the tooth expressing the predicted shape and size of the teeth after tooth decay, a distribution of the change in the thickness of the enamel layer over the tooth surface for a given point in the future may be derived from formulas derived at different regions of the tooth surface. The predicted digital 3D representation may then be generated by subtracting the distribution of the expected tooth wear from a recorded digital 3D representation. I.e. the expected tooth wear is locally derived by extrapolating the local development of the tooth wear over the surface such that the predicted digital 3D representation expresses the distribution of tooth wear over the patient's teeth. Such a predicted digital 3D representation of the teeth taking into account the expected wear on the teeth can be used e.g. in a virtual articulator used for evaluating the consequences of the tooth wear on the patient's occlusion and jaw movement. This can provide useful information for estimating when and if the patient is at risk of developing problems e.g. at the temporomandibular joint.

Likewise, when generating a predicted digital 3D representation of the tooth expressing the predicted reduction of the brightness of the teeth during tooth darkening a distribution of the change in the brightness of the tooth surface for a given point in the future may be derived from formulas derived at different regions of the tooth surface, in particular of the labial surface of the anterior teeth.

In some embodiments, the predicted digital 3D representation is visualized in a user interface according to an embodiment, where e.g. a virtual slider can be used to determine which point in time the predicted digital 3D representation is generated for.

In some embodiments, the formula is at least partly derived from general knowledge of teeth. The general knowledge may relate to the structure and/or development of teeth and/or development of caries in teeth. The structure can e.g. relate to an average enamel thickness for teeth.

The general knowledge may have been acquired from clinical studies, where the development of dental conditions for a large number of patient's teeth over time has been analyzed. Anatomical knowledge may e.g. be taken into account when the dental condition relates to relapse of teeth to an original arrangement after an orthodontic treatment has ended. An average rate at which such relapse occurs can be estimated from the general knowledge.

Especially when the development of the condition does not follow a constant rate, e.g. in cases where the development accelerates with time, using the general knowledge may provide a better estimate of the future development of the dental condition.

Clinical studies can provide knowledge relating to how fast caries will develop given the current color of the region or fluorescence profile over the tooth surface. Taking such general knowledge into account when deriving the formula provides that the prediction is biological founded and hence is more anatomically correct.

The general knowledge may also be provided by deep learning where the development of prior cases is deduced by the system and used for predicting the development for new patients.

The general knowledge may be introduced as an additional term in the formula.

In some embodiments, the method comprises aligning and comparing at least part of the obtained digital 3D representations. The change in the value of the parameter can then be determined based on the aligned digital 3D representations. When the digital 3D representations are aligned any change in the shape, size and position of the teeth and gingiva between the points of time where the digital 3D representations were acquired will become apparent. For instance, the change in the position of the gingival margin during gingiva recession or the movement of teeth during a relapse can directly be detected by such a comparison.

In some embodiments, the method comprises segmentation of at least some teeth in the digital 3D representations allowing for individual alignment of the corresponding teeth portions of the digital 3D representations. This is advantageous when determining e.g. tooth wear and there has been some teeth movement during the time elapsed between the points in time where the digital 3D representations were acquired. A comparison based on aligning un-segmented digital 3D representations will be sensitive to movements of the teeth during the elapsed time, such that e.g. tooth wear may be hidden by the tooth movement or tooth may erroneously be registered as tooth wear.

In some embodiments, the method comprises selecting one or more regions on one of the obtained digital 3D representations and identifying the corresponding region in digital 3D representations obtained at a different point in time. The parameter may then be determined for the selected region or regions in the different digital 3D representations such that the formula is derived for the selected region.

This may be advantageous when the value of the parameter differs over a single tooth or between the teeth. This is e.g. the case for tooth color or shade which often is lighter near the incisal edge/occlusal surface of the teeth than near the gingiva. Comparing the parameters in the selected regions of the teeth provides that the formula can be derived automatically for this particular region once the digital 3D representations are obtained.

Deriving the formula for a specific region on a tooth can also be advantageous when monitoring and predicting the development of caries in that region.

Disclosed is a user interface for predicting future development of a dental condition of a patient's set of teeth, wherein the user interface is configured for assisting a user in implementing a method comprising:

obtaining two or more digital 3D representations for the teeth recorded at different points in time;
deriving based on the obtained digital 3D representations a formula expressing the development of the dental condition as a function of time; and
predicting the future development of the condition based on the derived formula.

In some embodiments, the user interface comprises a virtual tool which when activated provides that an electronic data processing unit executes the instructions of a computer program product which derives the formula for predicting the future development of the condition based on the derived formula. The same or another virtual tool may estimate based on the derived formula when a threshold value of the parameter expected to be reached. The virtual tool(s) can be realized as a virtual push button(s) visualized in the user interface.

Disclosed is also a computer program product comprising computer readable instructions for causing an electronic data processing system to provide a digital tool configured for assisting a user in performing the method according to any of the embodiments, when said instructions are executed on the data processing system, and a computer program product, comprising a computer-readable medium having stored there on the program code means. The computer program product may be stored on a non-transitory computer readable medium.

Disclosed is a non-transitory computer readable medium storing thereon a computer program product, where said computer program product is configured for causing computer-assisted deriving of a formula expressing the development of a dental condition in terms of at least one parameter as a function of time, wherein the deriving comprises determining a change in at least one parameter from digital 3D representations of the patient's teeth obtained at different points in time such that the formula expresses the development of the dental condition in terms of the at least one parameter as a function of time Disclosed is a system for predicting future development of a dental condition of a patient's set of teeth, wherein the system comprises an electronic data processing unit and a non-transitory computer readable medium having stored thereon a computer program product comprising one or more instructions which when executed by the data processing unit provide a digital tool configured for assisting a user in performing a method of:

deriving a formula expressing the development of the dental condition in terms of at least one parameter as a function of time, where the formula is derived based on two or more digital 3D representations for the set of teeth recorded at different points in time; and
predicting the future development of the condition based on the derived formula.

The present invention relates to different aspects including the method, system, user interface and computer program product described above and in the following, and corresponding methods, systems, user interfaces and computer program products, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 1A-1C show workflows for embodiments.

DETAILED DESCRIPTION

In the following description, reference is made to the accompanying figures, which show by way of illustration how the invention may be practiced.

FIG. 1 show workflows for embodiments of the disclosed method for predicting future development of a dental condition of a patient's set of teeth. In FIG. 1A, the three general steps of a workflow 100 are illustrated. In step 101 two or more digital 3D representations for the teeth are obtained. The digital 3D representations are recorded at different points in time such that a change in a dental condition of the teeth can be detected and further development of the dental condition can be predicted based on the obtained digital 3D representations.

In step 102 a formula expressing the development of the dental condition in terms of at least one parameter as a function of time is derived from the obtained digital 3D representations.

In step 103, the future development of the condition is predicted based on the derived formula.

Figure 1B:
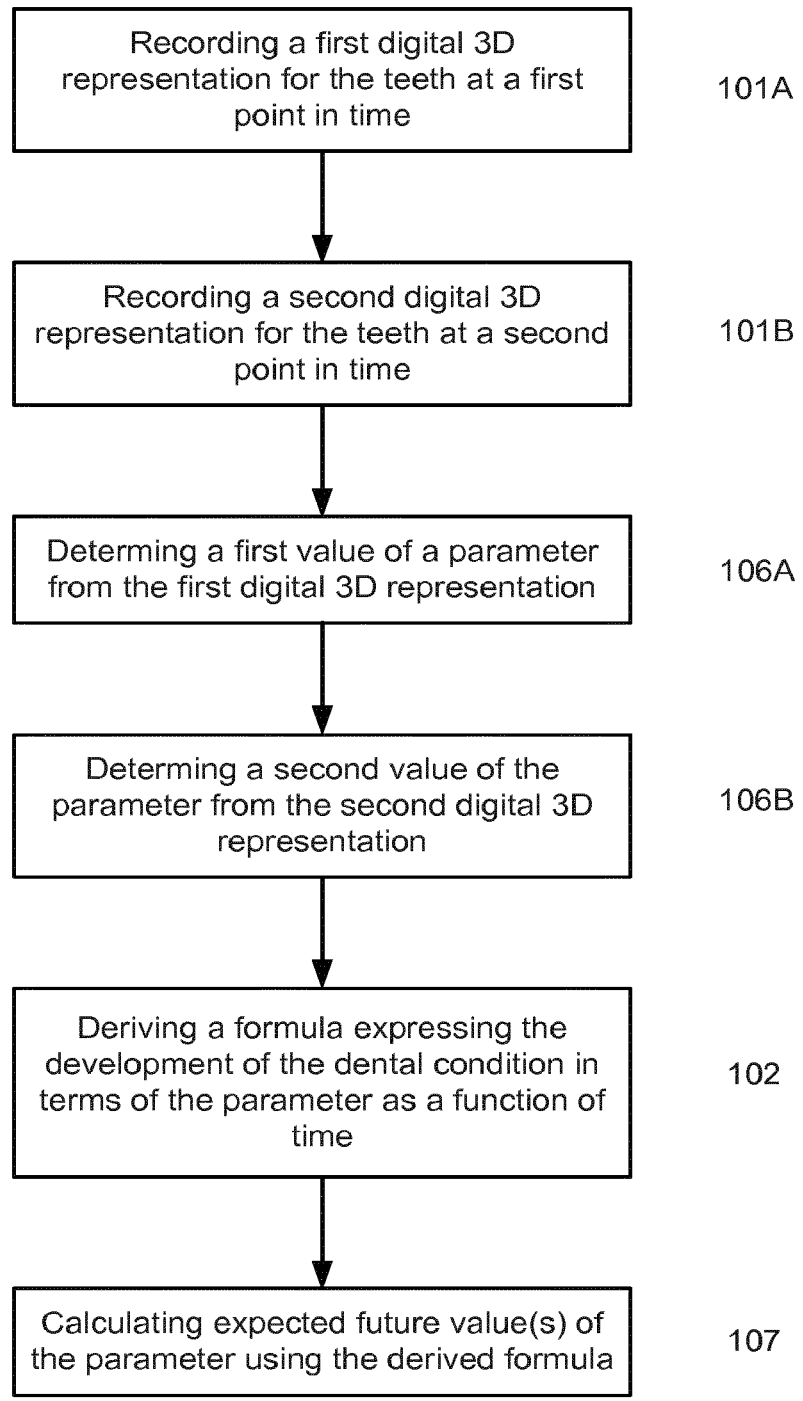

FIG. 1B illustrates the steps of a workflow 105 for predicting the future development of the dental condition using values of the parameter expressing a condition of the set of teeth determined from each single digital 3D representation. This may e.g. be the case when the parameter relates to the tooth color or shade and the dental condition relates to a darkening of the teeth over time.

In step 101A and 101B a first and a second digital 3D representation are recorded at a first and a second point in time, respectively. In step 106A a first value of the parameter is determined from the first digital 3D representation and in step 106B a second value of the parameter is determined from the second digital 3D representation.

The parameter can relate to e.g. the color or shade of the teeth, such as a color or shade in a selected region on a visible surface of one of the anterior teeth. Recording the color or shade at different points in time provides information regarding the change in the color or shade of the teeth with time, which e.g. can be caused by a darkening of the teeth.

Based on the determined first and second values of the parameter a formula expressing the development of the dental condition in terms of the parameter as a function of time is derived in step 102, and the derived formula is used to calculate the future values of the parameter in step 107 such that the development of the dental condition can be predicted.

Digital 3D representations for one or more additional points in time can be obtained and used for deriving the formula often improving the accuracy of the formula and the prediction it will provide.

The order of the steps shown in this figure only show one example. Often the parameter values will be determined when the digital 3D representation is obtained, such that the first value is determined before the second digital 3D representation is obtained. However, it may also be the case that the dentist realizes that a dental condition is under development and wishes to analyze previously obtained digital 3D representations for which this particular parameter was not determined.

Figure 1C:
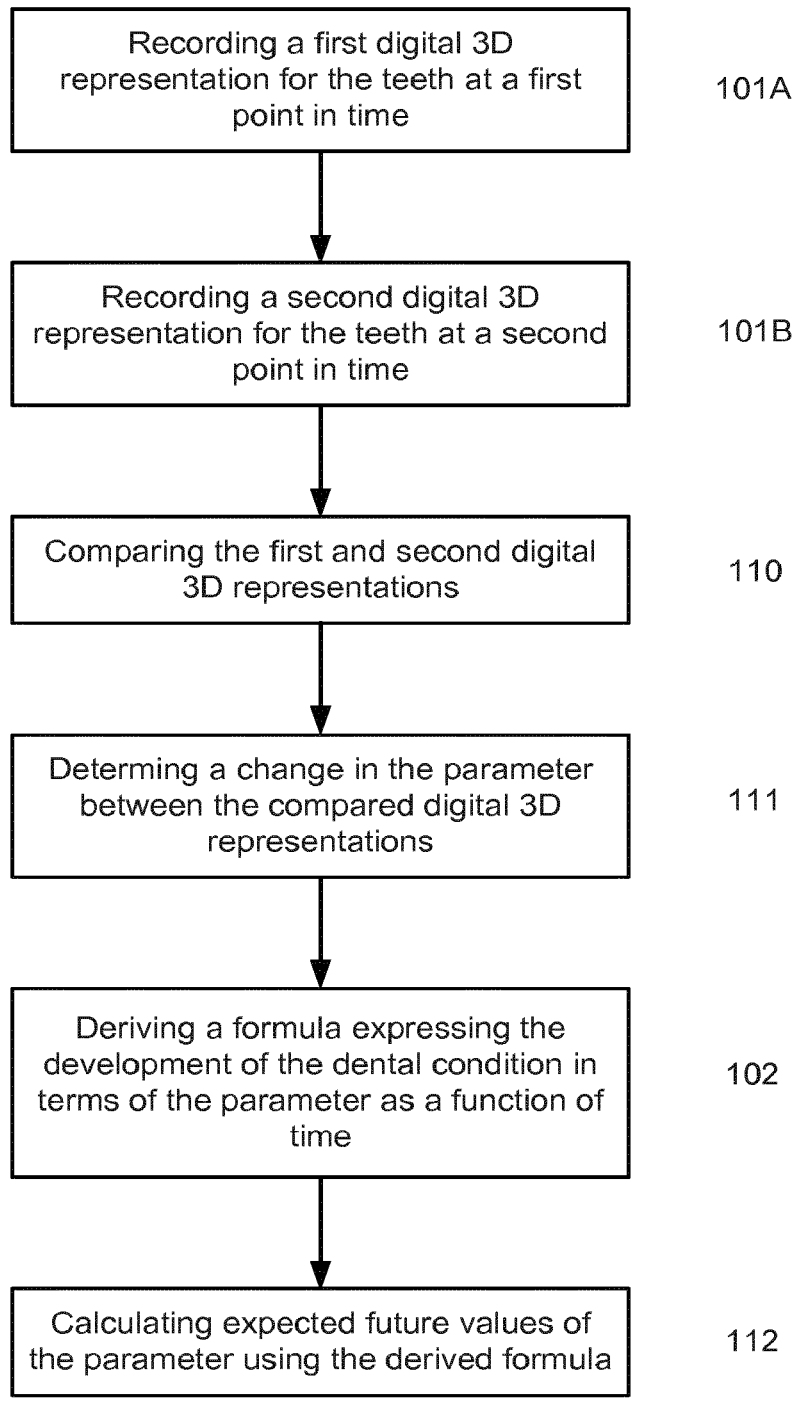

FIG. 1C illustrates the steps of a workflow 109 for predicting the future development of the dental condition when the formula is derived by determining changes in the parameter by comparing two or more digital 3D representations.

In step 101A and 101B a first and a second digital 3D representation are recorded at a first and a second point in time, respectively. In step 110 the first and second digital 3D representations are compared and in step 111 the change in the parameter for the time elapsed between the first and second point in time is determined based on the comparison. This approach may e.g. be advantageous when an absolute value of a parameter expression is difficult to determine from one digital 3D representation alone, such as e.g. when the dental condition relates to gingiva recession or tooth wear. Prior to the comparison, the teeth portions of the digital 3D representations may have been segmented from the remaining parts of the digital 3D representation and the segmented teeth locally aligned to provide that changes in the position of the teeth either can be determined precisely or do not interfere with a measure of e.g. tooth wear.

In step 102 the formula is derived based on the change in the parameter between the first and second digital 3D representations. Correlating the change in the parameter with the time elapsed between the first and second points in time provides an expected rate of change in the parameter over time.

The derived formula provides an estimate of the development of the dental condition based on the parameter. In step 112 the expected future value(s) of the parameter using the derived formula such that an estimate of the development of the dental condition can be provided.

For a series of digital 3D representations obtained at different points in time the change in the parameter can e.g. be determined by comparing all subsequent digital 3D representations recorded at later points in time with the first digital 3D representation. In case where the method is used for predicting tooth wear the change in the parameter will then most likely be continuously larger for each later point in time.

If the parameter is determined by comparing successive digital 3D representations the change in the parameter between successive points in time may both increase, remain the same or decrease depending on the duration between two successive points in time and the patient's behavior in that period of time. Based on the determined changes in the parameter an average value can be derived. E.g. when tooth wear is evaluated a comparison between subsequent digital 3D representations can be used to derived an average rate of the tooth wear (e.g. in units of mm per year) which then can be used to predict the future tooth wear unless preventive actions are taken and it can be estimated when the tooth wear has reached a threshold value linked to the expected thickness of the enamel layer.

FIG. 2 illustrates prediction of gingiva recession.

Figure 2A:
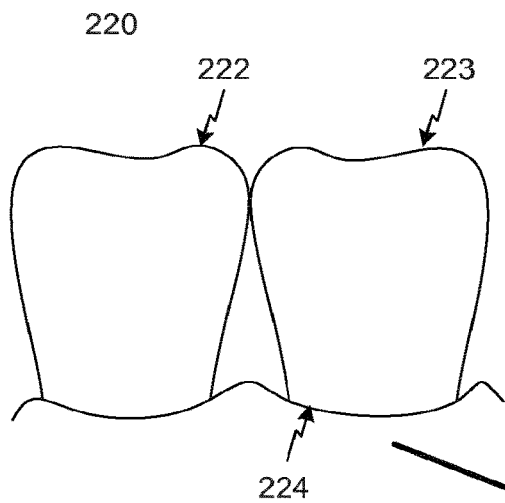
FIGS. 2A-2D illustrate prediction of gingiva recession
Figure 2B:
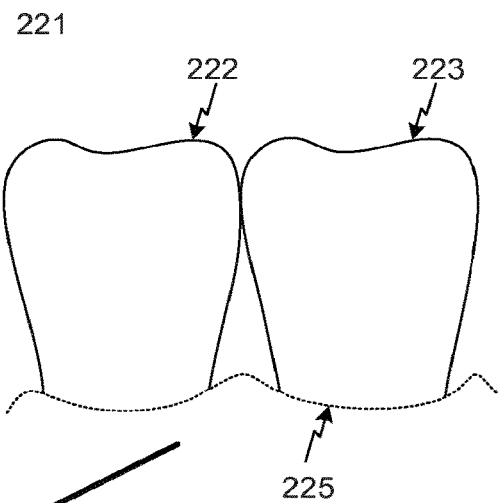
Figure 2C:
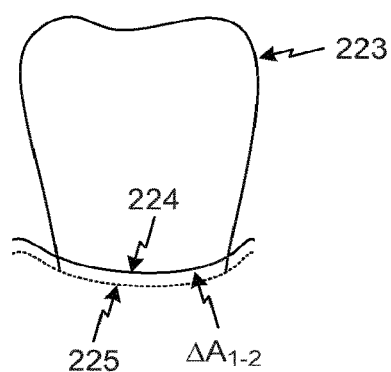

When the patient suffers from gingiva recession a gap may form between the teeth and gum line such that disease-causing bacteria can build up at the teeth. If left untreated, the supporting tissue and bone structures of the teeth can be severely damaged, and may ultimately result in tooth loss. The gingiva recession often happens slowly and the patient may not be aware of it. FIGS. 2A and 2B schematically show a first digital 3D representation 220 and a second digital 3D representation 221 both having geometrical data for the central anterior teeth 222, 223 in the patient's lower jaw, where the first and second digital 3D representations are obtained at a first and second point in time, respectively. The gingiva 224, 225 is identified in each digital 3D representation either from the geometry data or color data of the digital 3D representations. In order to accurately test for gingiva recession, the teeth portions of the digital 3D representations are segmented and the segmented teeth and nearby gingiva of the two digital 3D representations are aligned tooth by tooth. FIG. 2C shows the comparison with the segmented and aligned portions of the digital 3D representations relating to the left central anterior tooth 223 and the nearby gingiva. From this comparison the gingival recession between the first and the second point in time can be quantified as the area $\Delta A_{1-2}$ of the tooth region becoming exposed due to the recession. Alternatively, or in addition the gingival recession can be quantified by the maximum shift in the position of the gingival margin, or as an average value of the recession measured over the labial surface of the tooth 223.

Figure 2D:
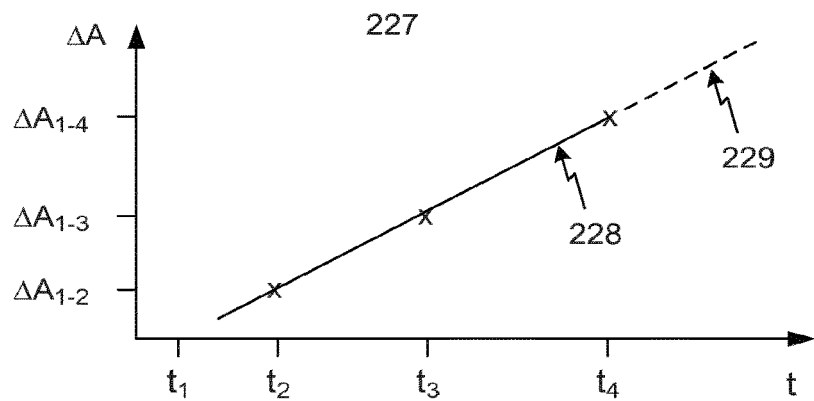

When a series of digital 3D representations are obtained for different points in time the comparison can be made for all the digital 3D representation, e.g. comparing all later digital 3D representations with the first digital 3D representation. For each point in time the gingiva recession relative to the first point in time is then determined and a formula expressing the gingiva recession as a function of time is derived. FIG. 2D shows a gingiva recession versus time graph 227 in which the values of the area exposed due to the gingiva recession ($\Delta A_{1-2}$, $\Delta A_{1-3}$, $\Delta A_{1-4}$) determined for a second, third and fourth point in time ($t_2$, $t_3$, $t_4$) relative to the first point in time ($t_1$) are plotted. Based on these values a formula expressing the gingiva recession as a function of time is derived. In this example the function 228 is linear with a slope indicating how fast the gingiva recession is progressing. The formula can be used to predict the future development of the gingiva recession by extrapolating into times beyond $t_4$ illustrated by the dashed line 229.

FIG. 3 illustrates prediction of tooth wear based on digital 3D representations of the teeth recorded over time.

Figure 3A:
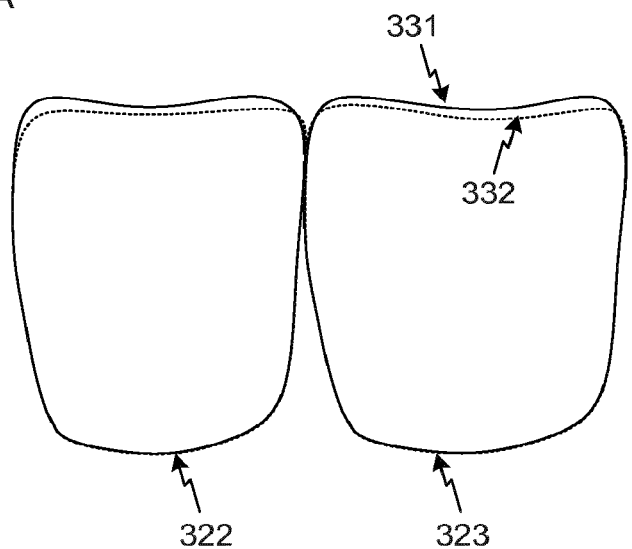
FIGS. 3A-3B illustrate prediction of tooth wear.

FIG. 3A shows a schematic of two digital 3D representations obtained for two of the molar teeth 322, 323 in a patient's lower jaw. During the period of time elapsed between the first and second points in time (where the first and second digital 3D representations were recorded) there has been a significant wear on the teeth. In order to provide a reliable measurement of the tooth wear, the teeth portions of the digital 3D representation are segmented and aligned on a tooth by tooth basis. When the segmented teeth are aligned a difference between the two digital 3D representations is seen at the occlusal surface, where the surface 332 in the second digital 3D representation lies below the surface 331 in the first digital 3D representation.

Accordingly tooth material has been removed from the tooth between the first and second point in time causing the tooth enamel to be thinner. The reduction in the thickness of the enamel can be quantified using a depth map which provides a local measure of the wear of the tooth over the occlusal surface. In a visualization of the teeth on a user interface the reduction in the depth of the enamel can e.g. be presented as a number to an operator when moving a computer mouse over the occlusal surface.

Figure 3B:
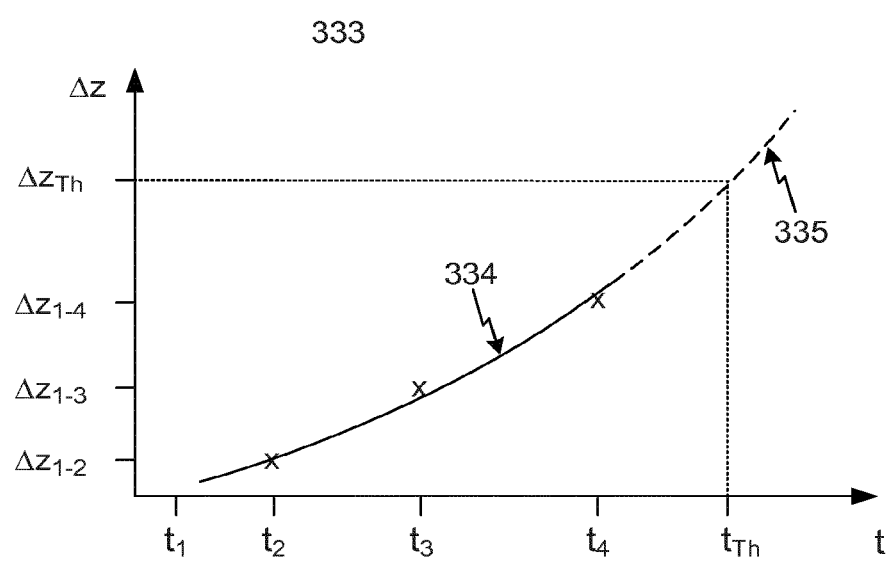

Comparing the second and further digital 3D representations obtained over time with the first digital 3D representation provides a measure for the reduction in the depth of the tooth enamel and a formula expressing the tooth wear as a function of time is derived. FIG. 3B shows a enamel reduction versus time graph 333 in which the values of the reduction ($\Delta z_{1-2}$, $\Delta z_{1-4}$) determined for a second, third and fourth point in time ($t_2$, $t_3$, $t_4$) relative to the first point in time ($t_1$) are plotted. Based on these values a formula expressing the reduction in the depth of the tooth enamel as a function of time is derived. In this example, the derived function has a slope which gradually increases with time such that the graph 334 is curved with an accelerated tooth wear. The formula can be used to predict the future development of the tooth wear by extrapolating into times beyond $t_4$ illustrated by the dashed line 335.

If a threshold value for the tooth wear is know, e.g. from X-ray or Optical Coherence Tomography (OCT) measurements indicating the thickness of the enamel layer at $t_1$, the formula can be used for estimating when the tooth wear reaches the threshold value. The average enamel thickness of normal teeth can also be determined from clinical studies and represent an important threshold since once the enamel is gone the patient will be very exposed to caries problems. As indicated in FIG. 3B the formula can predict a threshold time $t_{Th}$ at which the enamel in some parts of the tooth is expected to be gone unless preventive actions are taken.

The tooth wear can be described in terms of a distance map between the obtained digital 3D representations, such as between the first and the subsequent digital 3D representations, such that the tooth wear is derived relative to the first point in time.

When the distribution of the tooth wear over the tooth is determined the outcome of the prediction can be a digital 3D representation of the tooth expressing an expected form of the tooth in case the teeth wear progresses. This predicted digital 3D representation can be generated by subtracting the expected tooth wear from the first digital 3D representation, where the expected tooth wear is locally derived by extrapolating the local development of the tooth wear over the surface. Such a predicted digital 3D representation of the teeth taking into account the expected wear on the teeth can be used e.g. in a virtual articulator used for evaluating the consequences of the tooth wear on the patient's occlusion and jaw movement. This can provide useful information for estimating when and if the patient is at risk of developing problems e.g. at the temporomandibular joint.

Figure 4:
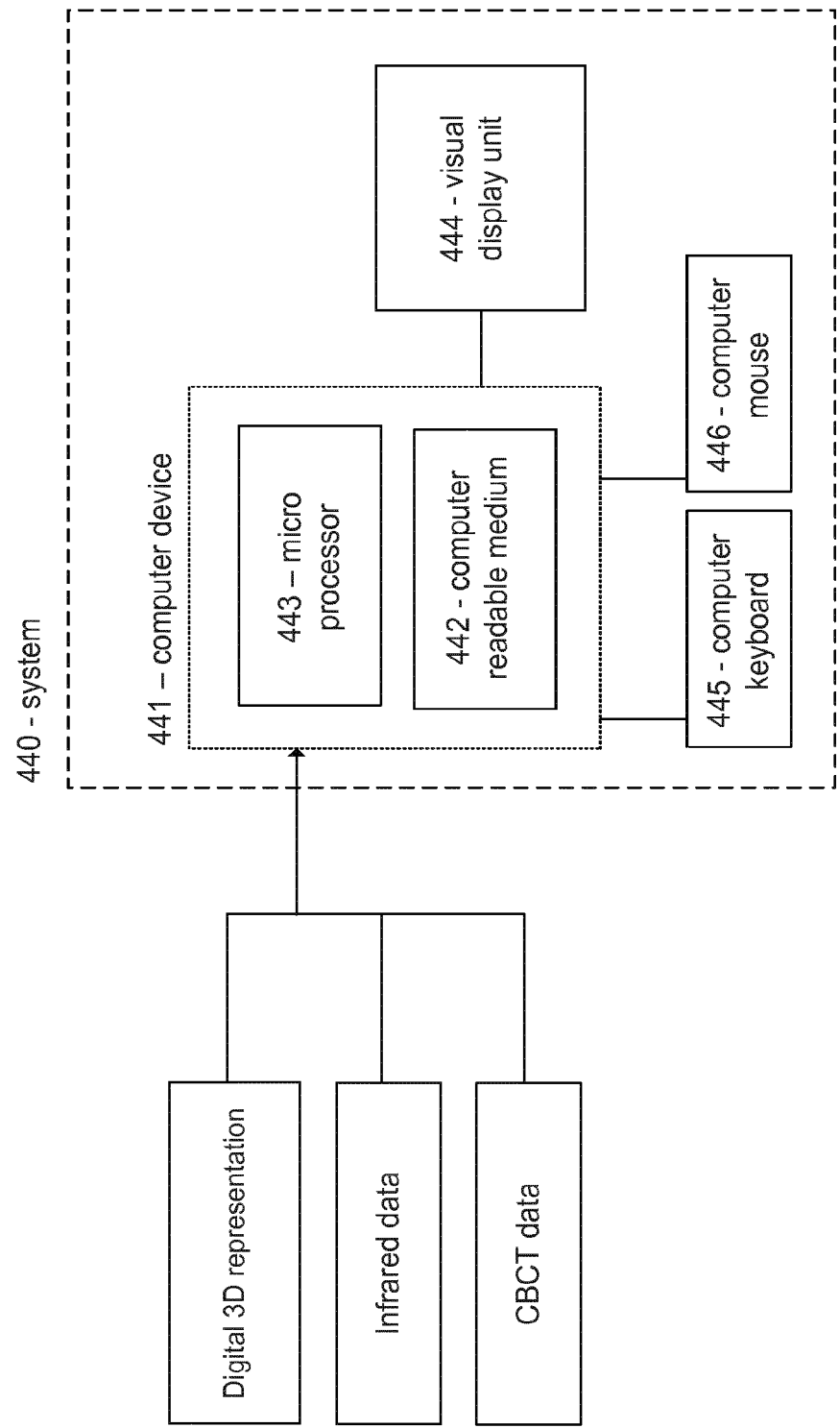
FIG. 4 shows a schematic of a system

FIG. 4 shows a schematic of a system according to an embodiment. The system 440 comprises a computer device 441 comprising a non-transitory computer readable medium 442 and an electronic data processing device in the form of a microprocessor 443. The system further comprises a visual display unit 444, a computer keyboard 445 and a computer mouse 446 for entering data and activating virtual buttons of a user interface visualized on the visual display unit 444. The visual display unit 444 can e.g. be a computer screen. Embedded on the non-transitory computer readable medium 442 is a computer program product with computer readable instructions which when executed by the microprocessor provides a digital tool that assists a user in performing the method for predicting the future development of the dental condition based on recorded digital 3D representations of the teeth.

The computer device 441 is capable of storing obtained digital 3D representations of the patient's teeth in the computer readable medium 442 and loading these into the microprocessor 443 for processing. The digital 3D representations can be obtained from a 3D color scanner, such as the 3Shape TRIOS 3 intra-oral scanner, which is capable of recording a digital 3D representation containing both geometrical data and color data for the teeth. Besides color and geometry data the digital 3D representation can also include diagnostic data, such fluorescence data obtained using an intra-oral scanner.

Additional diagnostic data can be recording using different types of diagnostic devices, such as an Infrared scanner, a fluorescence scanner, or a CBCT scanner for recording infrared, fluorescence, or CBCT data, respectively.

Using infrared light to interrogate the teeth has the advantage that the teeth are highly transparent at infrared wavelengths and that the infrared light can be scatted by caries infection. Infrared light is hence good for detecting interproximal caries which otherwise only can be detected from X-ray data.

The recorded diagnostic data are loaded into the computer readable medium 442 and analyzed using the microprocessor 443 to derive the parameter expressing the dental condition of the patient's teeth. The diagnostic data are visualized e.g. together with the digital 3D representation on the visual display unit 444.

If the diagnostic data and the digital 3D representation are not geometrically linked using e.g. markers appearing in both the system 441 is configured for allowing an operator to arrange the digital 3D representation and the diagnostic data according to the spatial arrangement which best reflects to anatomical correct arrangement. This is relevant when the spatial correlation between the digital 3D representation and the diagnostic data is needed but not known. This can e.g. be the case when the diagnostic data are infrared data which has been recorded independently of the digital 3D representation. The digital 3D representation and the diagnostic data can be moved relative to each other in three dimensions using e.g. a computer mouse to drag or rotate visualizations of the digital 3D representation and the diagnostic data on the visual display unit 444. When the operator is satisfied with the relative arrangement he activates a virtual push button in the user interface and the spatial relationship is stored in the computer readable medium 442.

When the diagnostic data are CBCT data they can often be aligned with the geometrical data of the digital 3D representation based on radiopaque markers providing signals in both the CBCT scan and the digital 3D representation.

Computer implemented algorithms for analyzing the diagnostic data to derive a parameter expressing tooth condition information for the patient's teeth, such as root and jaw-bone health, can also be stored on the computer readable medium 442.

The computer readable medium 442 can further store computer implemented algorithms for segmenting teeth from the digital 3D representation and identification of the individual teeth. When applied to the digital 3D representation the result is digital 3D models of the individual teeth where the corresponding teeth numbers are known. These digital models of the individual teeth can be stored on the computer readable medium 442 and be re-used at the next visit for the identification of individual teeth in a digital 3D representation recorded at the next visit.

When the spatial correlation between the digital 3D representation and the diagnostic data is known it is also known which tooth or teeth a given tooth condition parameter is derived for. Thereby the dentist will have a useful tool for evaluating the patient's dental situation and to determine which treatments can be applied to correct for any problems.

Figure 5:
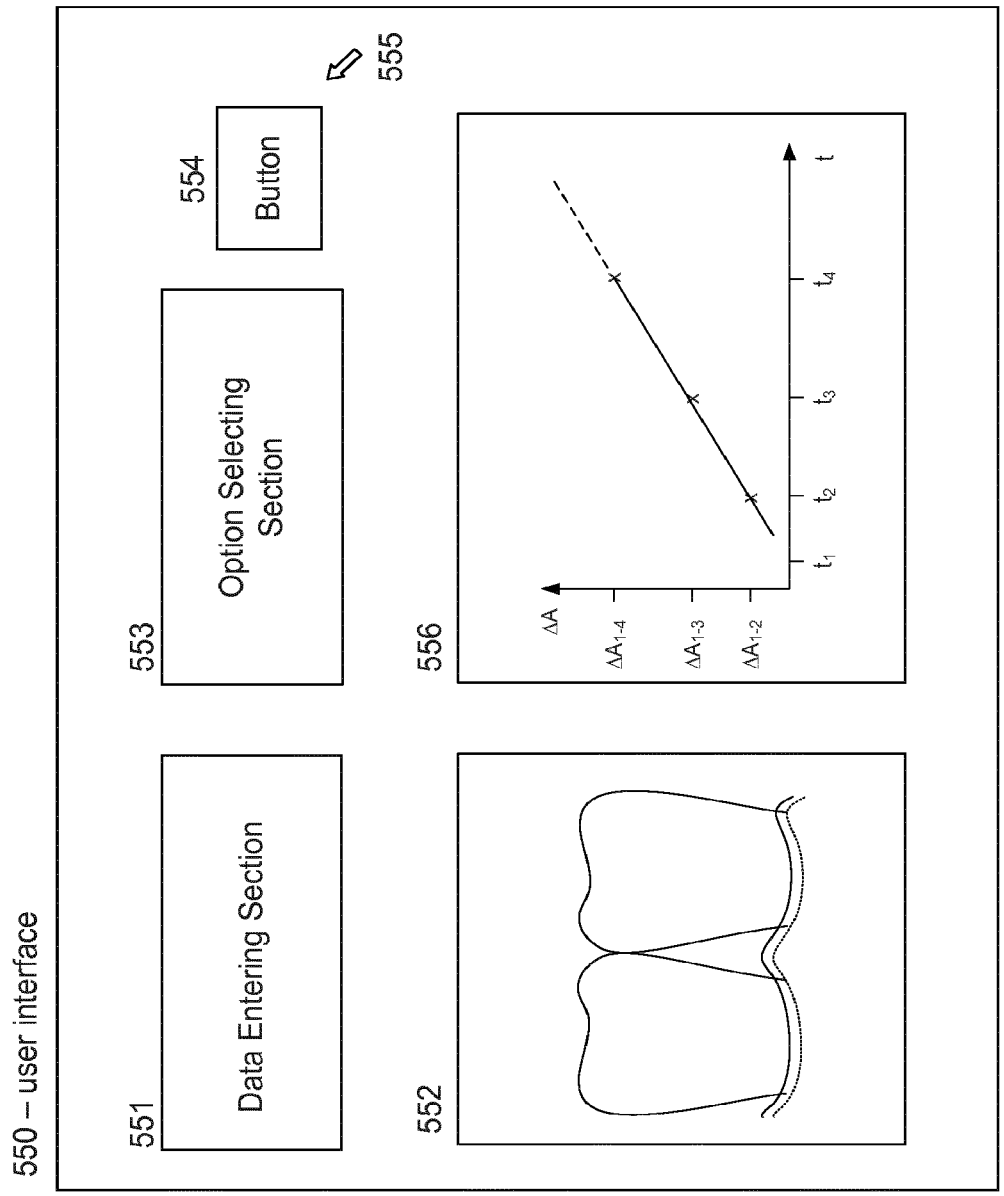
FIG. 5 shows a schematic of a user interface

FIG. 5 shows a schematic of a user interface.

The user interface 550 sketched in FIG. 5 has a Data Entering Section 551 for entering various data such as patent specific data and the digital 3D representations recorded for the patient. The recorded digital 3D representations are visualized in Visualization Section 552 which also may allow the operator to manually align the digital 3D representations or mark for which parts of the digital 3D representation the formula should be calculated. In the Option Selecting Section 553 is selected which parameter or dental condition is to be evaluated, which digital 3D representation forms the zero point for deriving the formula, how the values of the parameter are determined etc. When all relevant choices are made the virtual push button 554 is pressed using a mouse cursor 555 and a formula is derived for predicting the development of the parameter values and the dental condition over time. The derived formula is then visualized graphically in the Result Window 556. The user interface can be visualized on a visual display unit, such as a computer screen being part of a system configured for implementing the disclosed method.

FIG. 6 illustrates prediction of tooth darkening over time.

When the obtained digital 3D representations have color data for the teeth and gums, changes in the tooth color can be monitored and a formula expressing the darkening of teeth with time can be derived and used to predict continued future darkening.

Figure 6A:
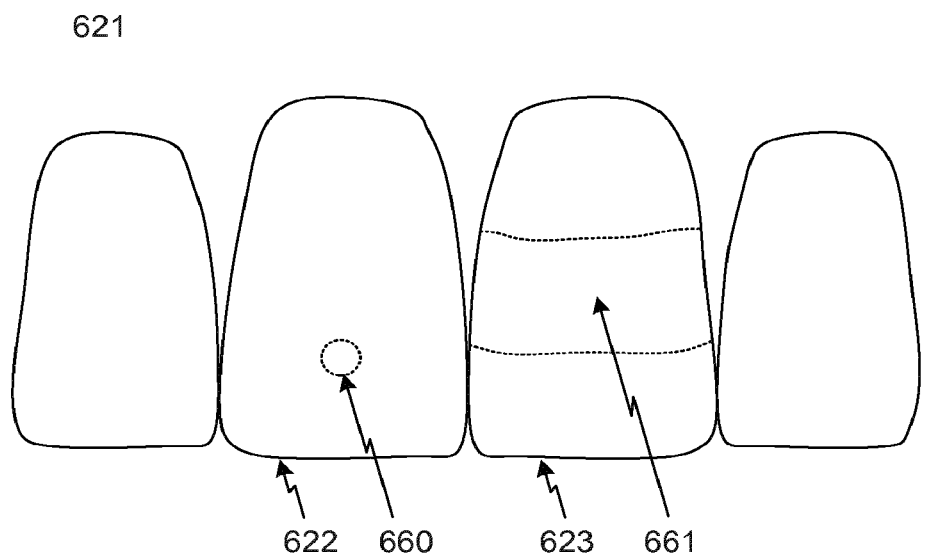
FIGS. 6A-6B illustrate prediction of tooth darkening.

FIG. 6A shows a second digital 3D representation 621 of the anterior teeth in the patient's upper jaw. The color normally varies over the surface of each tooth 622, 623, such that in order to provide an accurate prediction of color changes it is advantageous to compare the color data for the same tooth portion in the different digital 3D representations. FIG. 6A illustrates two ways of selecting which tooth portion is used in the comparison. One option is to define a relatively small portion of the tooth such as the portion 660 on tooth 622. Choosing such a small portion provides that local changes in the tooth color can be detected but also has the disadvantage that highly localized color changes or measurement uncertainty can cause that the predicted color changes are overestimated. An alternative approach is to average the color over a larger portion of the tooth, such as the band 661 extending horizontally across the tooth 623. This approach is in line with the normal coloring of natural teeth where the tooth normally is darker near the root and becomes progressively brighter towards the incisal edge. The color of a given portion of the tooth can be expressed in terms of different color systems, such as the L*a*b* color system, or as a shade value using e.g. the VITA 3D Mater shade system.

Aligning the digital 3D representations used for deriving the color changes such that the tooth surfaces of the digital 3D representation coincide provides that the tooth portion selected for color analysis in one the digital 3D representations readily can be identified in the other digital 3D representation(s). The selected portion can also be identified in the other digital 3D representations by determining the spatial relationship between the portion and a reference mark on the teeth, such as relative to three reference points selected at specific parts of the digital 3D representations. These reference points can e.g. be points on the teeth suitable for alignment of digital 3D representations, such as points on molar cusps and on the incisal edge of an anterior tooth.

Figure 6B:
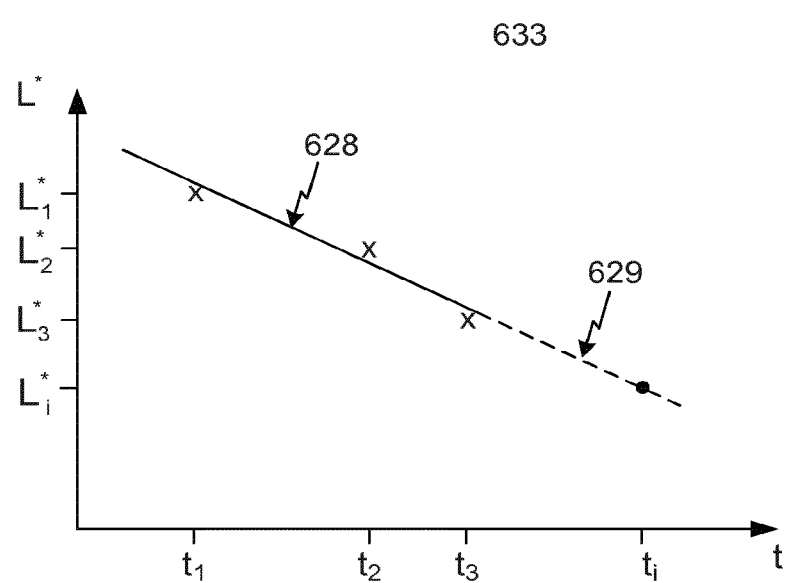

One way of monitoring and predicting darkening of teeth is based on the Lightness-value L* of the selected tooth portion. FIG. 6B shows a Lightness versus time graph 633 in which Lightness values ($L_1^*$, $L_2^*$, $L_3^*$) for a selected portion of a tooth measured for a first, second, and third point in time ($t_1$, $t_2$, $t_3$) are plotted. Based on the measured Lightness values a function for the development of the Lightness value over time is determined. In this example the function describes a linear curve 628, which can be extrapolated to future points in time, such that the Lightness value, $L_i^*$, for a later point in time, $t_i$, can be predicted.

A threshold value for the darkening of the teeth, i.e. the level of darkening the patient will accept. The formula can then provide an estimate of when the teeth has reached that point unless the patient changes behavior or a bleaching treatment is chosen.

Each tooth can also be divided into a number of relatively small portions together covering the entire tooth surface and a color difference map for the tooth can be determined by comparing the tooth color data of the digital 3D representations for each portion. The color difference can e.g. be measured in units of the L*a*b* color system such that the color difference map for each portion of the tooth expresses the difference in the L*, a* and b* values for that portion. The color difference map is aligned with the digital 3D representations such that when a mouse is moved over the tooth surface in a visualization of e.g. the first digital 3D representation, the change in the color values for this portion of the tooth surface can be displayed at the digital 3D representation for the portion where the mouse currently is located. When a formula predicting the changes in color and/or shade for each portion of the teeth is derived a predicted digital 3D representation including the predicted color or shade values can be generated for a future point in time. Such a predicted digital 3D representation can be visualized in a user interface where e.g. a virtual slider can be used to determine which point in time the predicted digital 3D representation is generated for.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

What is claimed is:

1. A method for determining gingival recession of a patient's set of teeth, wherein the method comprises:

obtaining a first digital 3D representation comprising data of anterior teeth at a first point in time;

obtaining a second digital 3D representation comprising data for the anterior teeth at a second point in time;

identifying gingiva in the first digital 3D representation and in the second digital 3D representation;

segmenting the anterior teeth in the first digital 3D representation and in the second digital 3D representation;

aligning the segmented anterior teeth of the first digital 3D representation with the segmented anterior teeth of the second digital 3D representation on a tooth by tooth basis;

determining a first gingival margin line between the segmented anterior teeth and the gingiva of the first digital 3D representation, and determining a second gingival margin line between the segmented anterior teeth and the gingiva of the second digital 3D representation;

comparing a distance between the first gingival margin line and the second gingival margin line; and quantifying the gingival recession based on the comparison.

2. The method according to claim 1, wherein the gingival recession is quantified by a maximum shift in a position of the first gingival margin line to a position of the second gingival margin line.

3. The system method according to claim 1, wherein the gingival recession is quantified by an average value of the gingival recession.

4. The method according to claim 2, wherein the gingival recession is quantified by the maximum shift in the position of the first gingival margin line to the position of the second gingival margin line measured over a labial surface.

5. The method according to claim 3, wherein the gingival recession is quantified by the average value of the gingival recession measured over a labial surface.

6. The method according to claim 1, further comprising:

deriving, based on the obtained digital 3D representations, a formula expressing the gingival recession as a function of time; and predicting future development of the gingival recession based on the derived formula;

where the predicting comprises using the derived formula to predict the point in time where the gingival recession is expected to reach a threshold value.

7. The method according to claim 6, further comprising generating a predicted digital 3D representation expressing a predicted configuration of the set of teeth and gingiva at a future point in time by applying the derived formula on a digital 3D representation of the set of teeth.

8. The method according to claim 7, wherein generating the predicted digital 3D representation comprises applying a distribution of locally derived formula for the development of the gingival recession with time.

9. The method according to claim 6, wherein the formula is derived from values of the gingival recession determined for each of the obtained digital 3D representations.

10. The method according to claim 1, further comprising selecting one or more regions on one of the obtained digital 3D representations and identifying the corresponding region in digital 3D representations obtained at a different point in time.

11. The method according to claim 10, wherein the gingival recession is determined for the selected one or more regions in the two digital 3D representations such that a formula is derived for the selected one or more regions.

12. The method according to claim 1, further comprising determining a value of the gingival recession for a portion of one tooth.

13. The method according to claim 1, further comprising determining and predicting a value of the gingival recession as an average value over a portion of one of the anterior teeth or over an entirety of the one anterior tooth.

14. A system for determining gingival recession of a patient's anterior teeth, the system comprising
an electronic data processing unit and a non-transitory computer readable medium having stored thereon a computer program product comprising one or more instructions which when executed by the electronic data processing unit provide a digital tool configured for assisting a user in performing a method of:
obtaining two or more digital 3D representations for the anterior teeth recorded at different points in time;
segmenting the anterior teeth in each of the two or more digital 3D representations;
aligning the segmented anterior teeth in each of the two or more digital 3D representations on a tooth by tooth basis;
determining gingival margin lines between the segmented anterior teeth and gingiva in each of the two or more digital 3D representations;
comparing a distance between two or more of the gingival margin lines; and
quantifying the gingival recession based on the comparison.

15. The system according to claim 14, wherein the method further comprises:
deriving a formula expressing the development of the gingival recession as a function of time, where the formula is derived based on the two or more digital 3D representations for the anterior teeth recorded at different points in time; and
predicting future development of the gingival recession based on the derived formula.

16. The system according to claim 15, wherein the predicting comprises using the derived formula to predict the point in time where the gingival recession is expected to reach a threshold value.

17. The system according to claim 14, wherein the gingival recession comprises a maximum shift in positions of the two or more of the gingival margin lines.

18. The system according to claim 14, wherein the gingival recession comprises an average value of the gingival recession measured over a labial surface.

19. A computer program product embodied in a non-transitory computer readable medium, the computer program product comprising computer readable program code being executable by a hardware data processing unit to cause the hardware data processing unit to:
obtaining two or more digital 3D representations for anterior teeth recorded at different points in time;
segmenting the anterior teeth in each of the two or more digital 3D representations;
aligning the segmented anterior teeth in each of the two or more digital 3D representations on a tooth by tooth basis;
determining gingival margin lines between the segmented anterior teeth and gingiva in each of the two or more digital 3D representations;
comparing a distance between two or more of the gingival margin lines; and
quantifying a gingival recession based on the comparison.

20. The computer program product according to claim 19, wherein the computer program product further causes the hardware data processing unit to:
deriving a formula expressing the development of the gingival recession as a function of time, where the formula is derived based on the two or more digital 3D representations for the anterior teeth recorded at different points in time; and
predicting future development of the gingival recession based on the derived formula.

21. The computer program product according to claim 20, the computer readable program code being executable by the hardware data processing unit to cause the hardware data processing unit to use the derived formula to predict the point in time where the gingival recession is expected to reach a threshold value.

22. The computer program product according to claim 19, wherein the gingival recession comprises a maximum shift in positions of the two or more of the gingival margin lines.

23. The computer program product according to claim 19, wherein the gingival recession comprises an average value of the gingival recession measured over a labial surface.

* * * * *